(12) United States Patent
Agano (10) Patent No.: US 7,786,458 B2
(45) Date of Patent: Aug. 31, 2010

(54) IMAGE READING METHOD AND APPARATUS

(75) Inventor: Toshitaka Agano, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 453 days.

(21) Appl. No.: 10/352,107

(22) Filed: Jan. 28, 2003

(65) Prior Publication Data

US 2003/0141469 A1 Jul. 31, 2003

(30) Foreign Application Priority Data

Jan. 28, 2002 (JP) .............................. 2002/017934

(51) Int. Cl.
G01N 23/04 (2006.01)
(52) U.S. Cl. ..................................... 250/591
(58) Field of Classification Search .................. 250/591
See application file for complete search history.

(56) References Cited

U.S. PATENT DOCUMENTS

| 4,803,359 | A | | 2/1989 | Hosoi et al. | |
|---|---|---|---|---|---|
| 4,975,772 | A | * | 12/1990 | Fujita | 348/607 |
| 5,530,238 | A | | 6/1996 | Meulenbrugge et al. | |
| 6,268,614 | B1 | | 7/2001 | Imai | |
| 6,376,857 | B1 | | 4/2002 | Imai | |
| 2002/0000528 | A1 | * | 1/2002 | Imai | 250/580 |

FOREIGN PATENT DOCUMENTS

| JP | 1-216290 | 8/1989 |
|---|---|---|
| JP | 2-164067 | 6/1990 |
| WO | WO 92/06501 | 4/1992 |

OTHER PUBLICATIONS

SPIE, vol. 1443 Medical Imaging v; Image Physics (1991), pp. 108-119.
"Material Parameters in Thick Hydogenated Amorphous Silicon Radiation Detectors", Lawrence Berkeley Laboratory, University of California, Berkeley, CA 94720.
Antonuk et al, "Signal noise, and readout considerations in the development of amorphous silicon photodiode arrays for radiotheraphy and diagnostic x-ray imaging", SPIE, vol. 1443 Medical Imaging v; Image Physics (1991), pp. 108-119.
Qureshi et al., "Material Parameters in Thick Hydogenated Amorphous Silicon Radiation Detectors", Lawrence Berkeley Laboratory, University of California, Berkeley, CA 94720 (1990, best estimated date).

* cited by examiner

Primary Examiner—David P Porta
Assistant Examiner—Shun Lee
(74) Attorney, Agent, or Firm—Sughrue Mion, PLLC (57) ABSTRACT

An image reading method and apparatus for reading an image signal by exposure to reading light L2 from a radiation solid-state detector, where radiation image information is recorded by exposure to recording light L1, suppresses degradation of image quality such as the S/N ratio of a reproduced image, the degradation being caused by an effect of charges which are produced by exposure to excessive radiation or the like and remains in the radiation solid-state detector. In the image reading method and apparatus, a past image signal read regarding past image information recorded in the radiation solid-state detector in the past, and an elapsed time from a time of recording the past image information in the radiation solid-state detector to a time of recording the current radiation image information are stored. The current image signal is then corrected based on the recorded past image information and the elapsed time.

12 Claims, 5 Drawing Sheets

FIG.2A

FIG.2B
X-Y SECTION

FIG.2C
X-Z SECTION

| $\Delta t_n$ | $x_n$ | $a_n$ |
|---|---|---|
| $\Delta t_1$ | $x_1$ | $a_1$ |
| $\Delta t_2$ | $x_2$ | $a_2$ |
| ⋮ | ⋮ | ⋮ |
| $\Delta t_n$ | $x_n$ | $a_n$ |

IMAGE READING METHOD AND APPARATUS

BACKGROUND OF THE INVENTION

1. Field of the Invention

The present invention relates to an image reading method and apparatus for reading image signals in accordance with image information from a solid-state detector, where the image information is recorded by exposure to an electromagnetic wave for recording.

2. Description of the Related Art

Currently, in radiography for the purpose of medical diagnosis or the like, there is known a radiation image recording and reading apparatus using a radiation solid-state detector for detecting radiation and outputting image signals which represent radiation image information. As the detector used in such an apparatus, various types of detectors have been proposed and put into practice.

For example, in terms of a charge generation process of converting radiation into charges, there are known radiation solid-state detectors of an optical conversion type (for example, U.S. Pat. No. 4,803,359, Japanese Unexamined Patent Publication No. 2(1990)-164067, PCT International Publication No. WO92/06501, and SPIE Vol. 1443 Medical Imaging V; Image Physics (1991), p. 108-119, etc.) and radiation solid-state detectors of a direct conversion type (MATERIAL PARAMETERS IN THICK HYDROGENATED AMORPHOUS SILICON RADIATION DETECTORS, Lawrence Berkeley Laboratory, University of California, Berkeley, Calif. 94720, Xerox PARC, Palo Alto, Calif. 94304, Metal/Amorphous Silicon Multilayer Radiation Detectors, IEEE TRANSACTIONS ON NUCLEAR SCIENCE, VOL. 36, NO. 2, APRIL 1989, Japanese Unexamined Patent Publication No. 1(1989)-216290, etc.). In the optical conversion type detectors, fluorescence emitted from a phosphor by exposure to radiation is detected by a photoelectric conversion device. Signal charges thereby obtained are once accumulated in an electric accumulator of the photoelectric conversion device, the accumulated charges are converted into an image signal (electric signal) and the image signal is outputted. In the direct conversion type detector, signal charges produced in a radiation conductive material by exposure to radiation are collected by a charge collection electrode and once accumulated in the electric accumulator. The accumulated charges are then converted into an electric signal and the electric signal is outputted.

In terms of a charge reading process of reading out the accumulated charges, there are known radiation solid-state detectors of a TFT (thin film transistor) reading type which read out the charges by scanning and driving TFTs connected to the electric accumulators, radiation solid-state detectors of an optical reading type which read out the charges by irradiating reading light (reading electromagnetic wave) on the radiation detectors, and the like.

There has also been proposed radiation solid-state detectors of an improved direct conversion type in U.S. Pat. Nos. 6,268,614 and 6,376,857. The radiation solid-state detectors of the improved direct conversion type employ a combination of the direct conversion type and the optical reading type. The radiation solid-state detector thereof includes a first electrode layer transparent with respect to recording radiation; a recording photoconductive layer which exhibits photoconductivity when exposed to the recording radiation transmitted through the first electrode layer; a charge transport layer which acts substantially as a insulator for charges of the same polarity as that of the charges accumulated in the first electrode layer and acts substantially as a conductor for charges of the opposite polarity to the same; a treading photoconductive layer which exhibits photoconductivity when exposed to the reading electromagnetic wave; and a second electrode layer transparent with respect to the reading electromagnetic wave, which are laminated in this order. Latent image charges bearing the image information are accumulated at the interface of the recording photoconductive layer and the charge transport layer.

As the method of reading the latent image charges in the radiation solid-state detector of the improved direct conversion type, the following methods are known. In one method, the second electrode is a flat plate, and the latent image charges are detected by scanning the second electrode layer with a spot-like reading light such as a laser beam. In another method, the second electrode is composed of a comb-teeth shaped stripe electrode, and the latent image charges are detected by scanning the second electrode layer with a linear light source in a longitudinal direction of the stripe electrode, the linear light source extending in a direction approximately perpendicular to the longitudinal direction of the stripe electrode.

In the optical reading method, the signal read from the flat plate electrode or the stripe electrode is obtained as pixel signals by sampling or the like. A region corresponding to the pixel signal represents a pixel in the radiation solid-state detector. In the TFT reading method, since the signal outputted from each transistor is read as the pixel signal, each transistor represents a pixel in the radiation solid-state detector.

A reproduced image is constituted based on an image signal composed of the pixel signals obtained as described above and provided for image diagnosis by display on a monitor or the like.

Here, the radiation solid-state detector as described above can repeatedly record the radiation image information and read the image signal in accordance with the radiation image information.

However, in the radiation solid-state detector as described above, the following problem occurs. If the radiation solid-state detector is exposed to radiation of excessive energy in recording of the radiation image, the sensitivity is lowered in a portion exposed to the radiation of excessive energy in recording and reading of the next radiation image. This is because the latent image charges produced by exposure to the radiation of excessive energy are not entirely read off and remains in the recording photoconductive layer as residual charges. The residual charges decrease the intensity of an electric field formed between the first electrode layer and the second electrode layer and decrease a charge conversion efficiency in the recording photoconductive layer. In the reading, the residual charges may also decrease a reading efficiency in the reading photoconductive layer. The decrease in the charge conversion efficiency and the decrease in the reading efficiency cause degradation of the S/N ratio of the reproduced image. The number of residual charges decreases over time, but a long period of time is required until the effect thereof is decreased to a negligible degree.

Not only in the radiation solid-state detector where the radiation image is recorded by converting radiation into charges, but also in the radiation solid-state detector where fluorescence is emitted by exposure to radiation and the radiation image is recorded by detecting the fluorescence, an efficiency of converting radiation into fluorescence is decreased by exposure to the excessive radiation, and the degradation of the image quality such as the S/N ratio of the image is caused similarly to the above radiation solid-state detector.

SUMMARY OF THE INVENTION

In light of the above described problem, an object of the present invention is to provide an image reading method and an image reading apparatus for suppressing degradation of image quality such as the S/N ratio of a reproduced image caused by the effect of residual charges which are produced by exposure to excessive radiation or the like and that remains in a radiation solid-state detector or the like.

In an image reading method for reading an image signal in accordance with image information from a solid-state detector, where the image information is recorded by exposure to a recording electromagnetic wave bearing the image information, the image reading method according to the present invention includes the steps of storing a past image signal read for past image information which is recorded in the solid-state detector before the image information is recorded in the solid-state detector, and storing a time T1 as a time of recording the past image information in the solid-state detector or a time of reading the past image information from the solid-state detector; acquiring a time T2 as a time of recording the current image information; calculating an elapsed time from the time of recording the past image information or the time of reading the past image information to the time of recording the current image information based on the time T1 and the time T2; and correcting the current image signal based on the past image signal and the elapsed time.

Here, the above described "recording electromagnetic wave" means, for example, radiation.

With respect to the above described "correcting the current image signal based on the past image signal and the elapsed time", in a case where the interval from the time of recording the past image information in the solid-state detector to the time of reading the same from the solid-state detector is short and the amount of loss of the recorded past image information during the interval is negligible, the correction is performed by using the time period from the time of recording the past image information to the solid-state detector or the time of reading the past image information from the solid-state detector, to the time of recording the current image information as the elapsed time. In a case where the interval from the time of recording the past image information in the solid-state detector to the time of reading the same from the solid-state detector is long and the amount of loss of the recorded past image information during the interval is not negligible, the correction is performed by using the time period from the time of recording the past image information in the solid-state detector to the time of recording the current image information in the solid-state detector as the elapsed time.

With respect to the above described "acquiring a time T2", the time T2 may be stored in the memory means when necessary.

In an image reading apparatus provided with a solid-state detector for accumulating charges produced by exposure to a recording electromagnetic wave bearing image information to record the image information, and a reading means for reading image signal in accordance with the image information recorded in the solid-state detector, an image reading apparatus according to the present invention includes a memory means, an elapsed time calculation means, and a correction means. The memory means stores a past image signal read regarding past image information, which is recorded in the solid-state detector before the current image information is recorded in the solid-state detector, and a time T1 as a time of recording the past image information in the solid-state detector or a time of reading the same from the solid-state detector. The elapsed time calculation means acquires a time T2 as a time of recording the current image information and calculates an elapsed time from the time of recording the past image information or the time of reading the same to the time of recording the current image information based on the time T1 and the time T2. The correction means corrects the current image signal based on the past image signal stored in the memory means and the elapsed time.

The correction means can be designed to calculate a certain coefficient based on the past image signal and the elapsed time and to correct the current image signal based on the certain coefficient and the past image signal.

Here, the decrease rate of the charges remaining in the solid-state detector over time varies depending on the size of the past image signal and is not constant. Therefore, it is desirable to correct the current image signal by calculating the certain coefficient in accordance with the above rate based on the past image signal and the elapsed time, and then calculating a signal size in accordance with residual charges in the recording time of the above described image information based on the coefficient and the past image signal.

The memory means stores past image signals regarding a plurality of pieces of past image information recorded at different times and the time T1's for the respective past image signals; the elapsed time calculation means calculates a plurality of elapsed times from the times of recording the plurality of pieces of past image information or the times of reading the same of past image information to the time of recording the image information based on the plurality of time T1's and the time T2; and the correction means corrects the current image signal based on the plurality of past image signals and the respective elapsed times.

Here, with respect to the above described "a plurality of pieces of past image information recorded at different times", objects of the images may be either same or different.

The correction means calculates the certain coefficients for each of the plurality of pieces of past image information based on the past image signals and the elapsed times, and corrects the current image signal based on the coefficients and the past image signals in accordance with the coefficients.

The reading means may include a linearly extending light source; a scanning mechanism for performing scanning with the linear light source in a direction substantially orthogonal to a longitudinal direction of the linear light source; and a stripe electrode including a plurality of linear electrodes arranged in the longitudinal direction. The linear electrodes linearly extend and take out charges produced by scanning. The scanning is performed with the linear light source in the substantially orthogonal direction by the scanning mechanism.

In addition, the reading means may include a number of TFT switches for taking out the charges as the image signal; and a control unit for controlling the TFT switches.

According to the image reading method and apparatus of the present invention, the past image signal read for the past image information, which is recorded in the radiation solid-state detector before the current image information is recorded in the solid-state detector, and the time T1 as the time of recording the past image information in the radiation solid-state detector or the time of reading the same from the solid-state detector are stored. The time T2 as the time of recording the above described image information is acquired. Based on the time T1 and the time T2, the elapsed time from the recording time of the past image information or the reading time thereof to the recording time of the above described image information is calculated. The current image signal is then corrected based on the past image signal and the elapsed time. Accordingly, it is possible to suppress degradation of the image quality such as the S/N ratio of the reproduced image, the degradation being caused by the effect of the charges which are produced by exposure to excessive radiation or the like and remains in the radiation solid-state detector in recording the past radiation image information.

In the case where the correction means calculates the certain coefficient based on the past image signal and the elapsed time and corrects the current image signal based on the coefficient and the past image signal, the signal size in accordance with the remaining charges in recording the image information can be calculated more accurately, and thus more accurate correction can be performed.

In the case where the memory means stores past image signals regarding the plurality of pieces of past image information recorded at different times and time $T1$'s for the respective past image signals, the elapsed time calculation means calculates a plurality of elapsed times from the times of recording the plurality of pieces of past image information or the times of reading the same to the time of recording the current image information based on the time $T1$'s and the time $T2$; and the correction means corrects the current image signal based on the plurality of past image signals and the plurality of elapsed times, the effect by the above described residual charges can be suppressed even when the solid-state detector is repeatedly used.

The correction means calculates the certain coefficients based on the past image signals and the respective elapsed times for the plurality of pieces of past image information recorded at the different times, and corrects the current image signal based on the plurality of past image signals and the plurality of elapsed times, and thus more accurate correction can be performed even when the solid-state detector is repeatedly used.

DESCRIPTION OF THE PREFERRED EMBODIMENT

Figure 1:
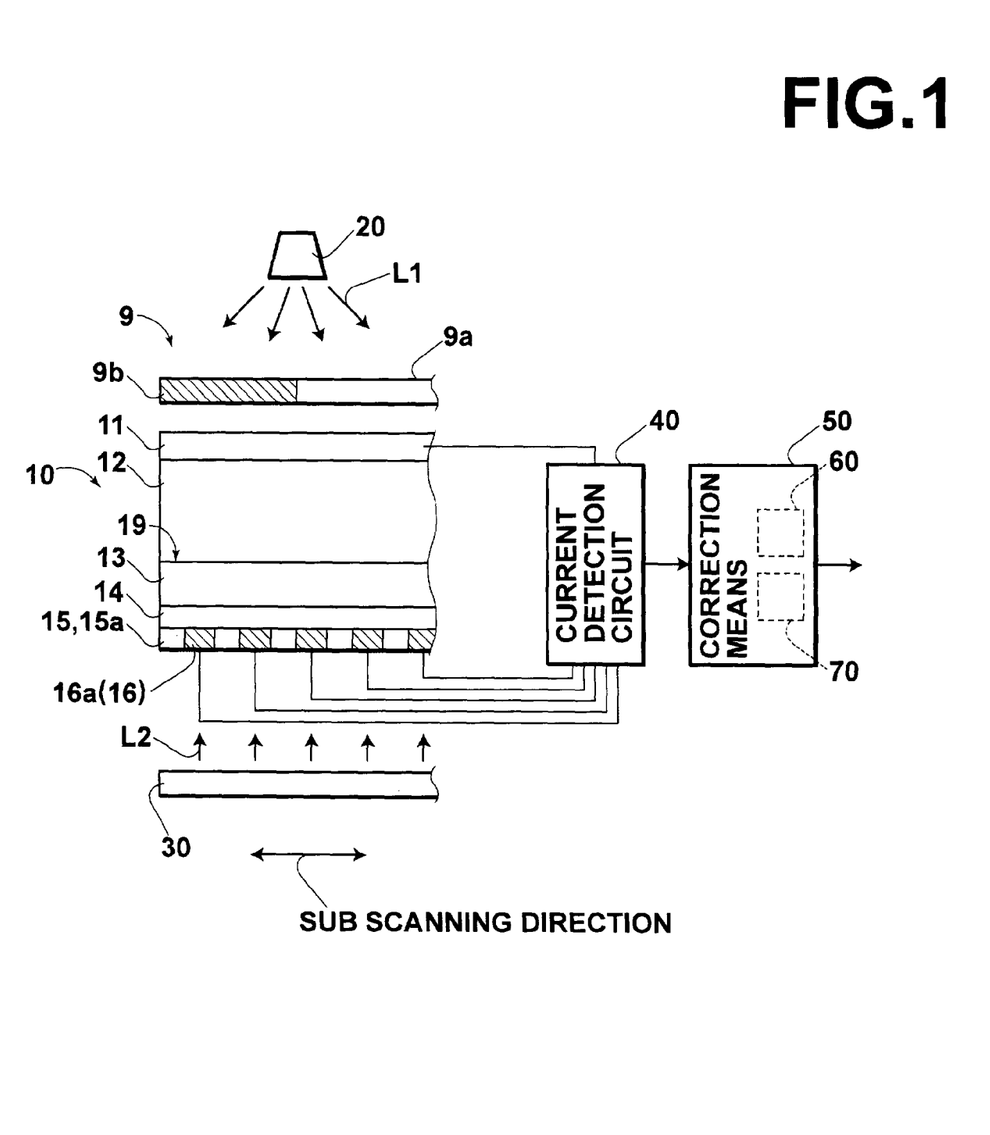
FIG. 1 is a schematic view showing a radiation image recording and reading apparatus to which a first embodiment of an image reading apparatus according to the present invention is applied.
Figure 2A:
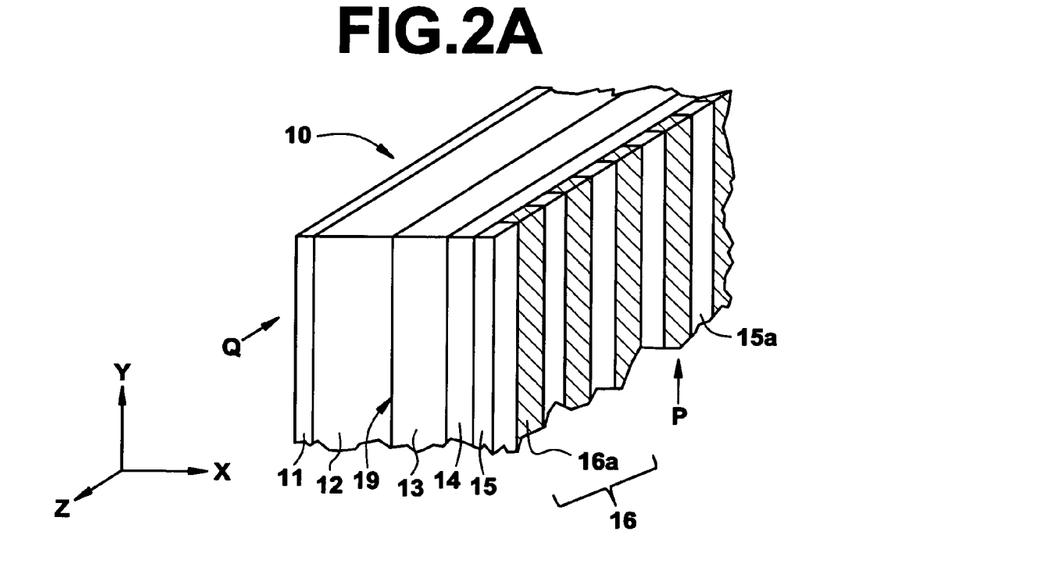
FIG. 2A is a perspective view showing a radiation solid-state detector for use in the radiation image recording and reading apparatus shown in FIG. 1.
Figure 2B:
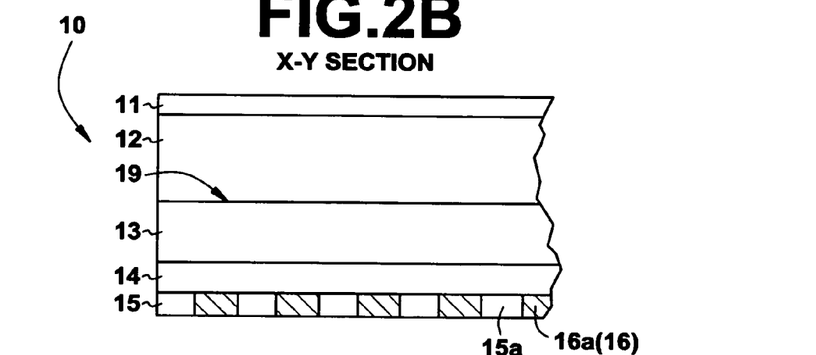
FIG. 2B is an X-Z sectional view of a portion indicated by an arrow Q.
Figure 2C:
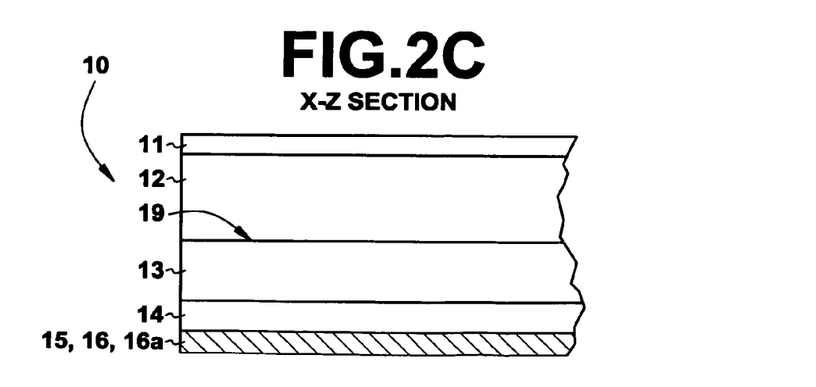
FIG. 2C is an X-Y sectional view of a portion indicated by an arrow P.

A description will be made below for an embodiment of the present invention with reference to the drawings. FIG. 1 is a schematic view showing a radiation image recording and reading apparatus to which an embodiment of an image reading apparatus carrying out an image reading method according to the present invention is applied. FIGS. 2A to 2C are schematic views showing a radiation solid-state detector used in the embodiment. Specifically, FIG. 2A is a perspective view thereof. FIG. 2B is an X-Z sectional view of a portion indicated by an arrow Q. FIG. 2C is an X-Y sectional view of a portion indicated by an arrow P.

First, a description will be made for a radiation solid-state detector 10 for use in the present radiation image recording and reading apparatus. The radiation solid-state detector 10 includes a first electrode layer 11, a recording photoconductive layer 12, a charge transport layer 13, a reading photoconductive layer 14, and a second electrode layer 15, which are laminated in this order. The first electrode layer 11 transmits a recording electromagnetic wave L1 (for example, radiation such as an X-ray, hereinafter, referred to as recording light). The recording photoconductive layer 12 exhibits conductivity when exposed to the recording light L1 transmitted through the first electrode layer 11. The charge transport layer 13 acts substantially as an insulator for latent image charges (for example, negative charges) and acts substantially as a conductor for transport charges (positive charges in the above example) of the opposite polarity to that of the latent image charges. The reading photoconductive layer 14 exhibits conductivity when exposed to an electromagnetic wave L2 for reading (hereinafter, referred to as reading light). The second electrode layer 15 transmits the reading light L2. In the radiation solid-state detector 10, the above layers are sequentially formed starting from the second electrode layer 15 on a supporting material that transmits the reading light L2. The supporting material is not shown in the drawings.

Materials suitable for the recording photoconductive layer 12 are photoconductive materials mainly composed of at least one of amorphous selenium (a-Se), lead (II) oxide such as PbO, lead (II) iodide such as $PbI_2$, $Bi_{12}(Ge, Si)O_{20}$, $Bi_2I_3$/organic polymer nanocomposite, and the like.

Preferably, the charge transport layer 13 has a difference as large as possible between mobility of the negative charges placed in the first electrode layer 11 and mobility of the positive charges as the opposite polarity thereto (for example, not less than $10^2$, and desirably not less than $10^3$). For example, materials suitable for the charge transport layer 13 are organic compounds such as poly-N-vinylcarbazole (PVK), N,N'-diphenyl-N,N'-bis(3-methylphenyl)-[1,1'-biphenyl]-4,4'-diamine (TPD) and discotic liquid crystal, TPD dispersed in a polymer (polycarbonate, polystyrene, PVK), a semiconductor material such as a-Se doped with Cl of 10 to 200 ppm, and the like. Particularly, the organic compounds (PVK, TPD, discotic liquid crystal, etc.) are preferred because of the insensitivity to light thereof. Moreover, the above described organic compounds generally have small dielectric constants. Accordingly, capacity of the charge transport layer 13 and the reading photoconductive layer 14 is decreased, and an efficiency of taking out signals in the reading can be increased. The "insensitivity to light" means that conductivity is hardly exhibited on exposure to the recording light L1 or the reading light L2.

Materials suitable for the reading photoconductive layer 14 are photoconductive materials mainly composed of at least one of a-Se, Se—Te, Se—As—Te, nonmetal phthalocyanine, metal phthalocyanine such as MgPc (Magnesium phthalocyanine), VOPc (phase II of vanadyl phthalocyanine), and CuPc (copper phthalocyanine), and the like.

In order to sufficiently absorb the reading light L1 in the recording photoconductivity layer 12, the thickness thereof is preferably not less than 50 μm and not more than 1000 μm, and is about 500 μm in this example. The total thickness of the charge transport layer 13 and the photoconductive layer 14 is desirably not more than half the thickness of the recording photoconductive layer 12. Moreover, since the thinner the total thickness is, the better the response in the reading, the total thickness of the charge transport layer 13 and the photoconductive layer 14 is preferably not more than 1/10 of the recording photoconductivity layer 12, further preferably, not more than 1/20 thereof.

For the first and second electrode layers 11 and 15, for example, Nesa film obtained by coating a transparent glass with a conductive material is suitable.

An electrode in the second electrode layer 15 is formed as a stripe electrode 16 including a number of elements (linear electrodes) 16a arranged in a stripe configuration. Space 15a between the elements 16a is filled with a polymer material such as polyethylene containing some amount of pigment such as carbon black dispersed and designed to have a light blocking effect on the reading light L2.

Next, the radiation image recording and reading apparatus of the embodiment will be described. FIG. 1 is a constitutional view schematically showing the radiation image recording and reading apparatus of the embodiment, showing an XZ sectional view of the radiation solid-state detector 10 and a current detection circuit 40 in detail.

The present radiation image recording and reading apparatus includes the radiation solid-state detector 10, a recording light irradiation means 20, a reading light irradiation means 30, the current detection circuit 40, and a correction means 50.

An object 9 is arranged above the first electrode layer 11. The object 9 includes a transparent part 9a transparent with respect to the reading light L1 and a light blocking part 9b opaque with respect to the recording light L1. The recording light irradiation means 20 irradiates the recording light L1 uniformly on the object 9.

The reading light irradiation means 30 performs scanning exposure with the reading light L2, which is substantially uniform in a line shape, in a longitudinal direction (sub scanning direction in FIG. 1) of each element 16a of the stripe electrode 16, and in a direction substantially orthogonal to the longitudinal direction (sub scanning direction). In the scanning exposure, the reading light irradiation means 30 may irradiate either continuous light or pulse light.

The current detection circuit 40 obtains an image signal at a level in accordance with a quantity of the latent image charges accumulated in an electric accumulator 19. The current detection circuit 40 includes a number of current detection amplifiers connected to the respective elements 16a of the stripe electrode 16.

Figure 4:
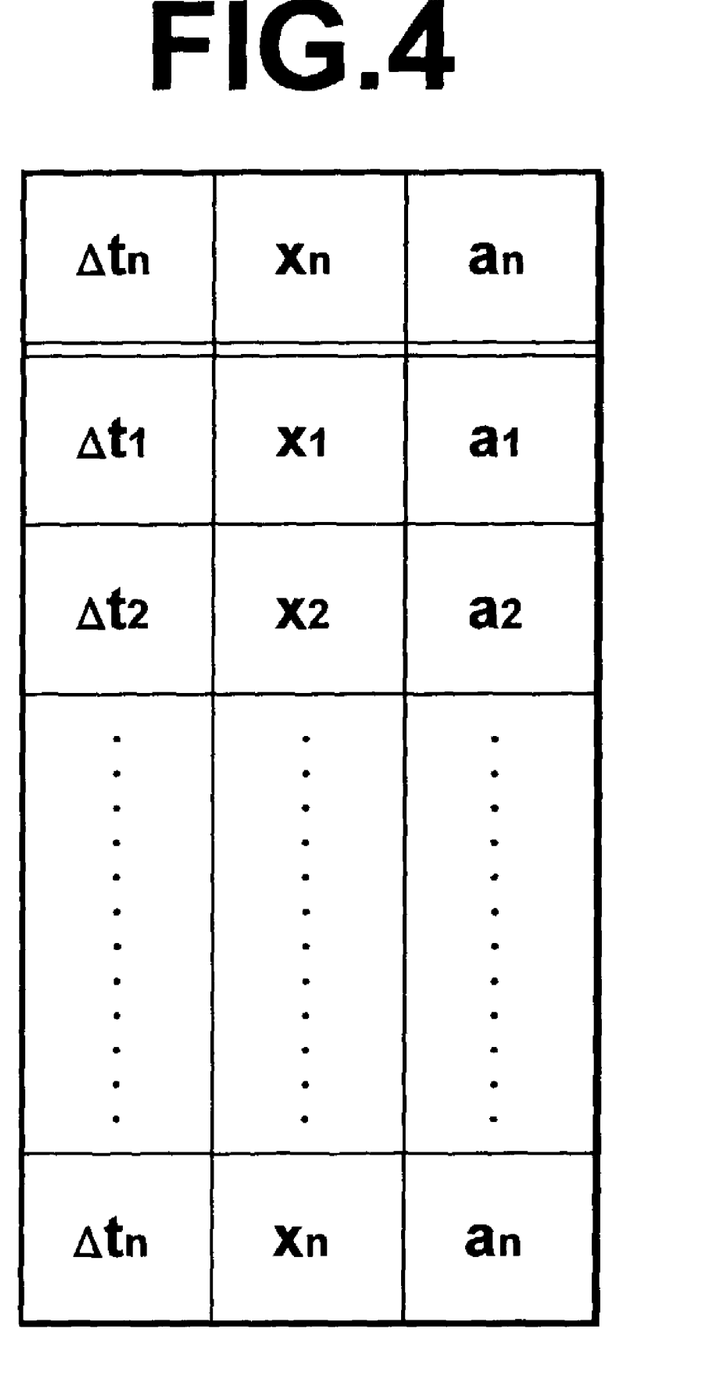
FIG. 4 is a view showing an LUT referred to in correction processing in a correction means.

The correction means 50 stores a pixel signal outputted from the above described current detection circuit 40 in a memory for each pixel. The correction means 50 performs correction processing for the stored pixel signal of each pixel to correct for an effect of the charges remaining in the radiation solid-state detector by use of past image information recorded in the radiation solid-state detector in the past. The correction means 50 includes a memory means 60. The memory means 60 stores past image signals regarding a plurality of pieces of past image information recorded in the radiation solid-state detector 10 in the past and a plurality of time T1's when the above described plurality of pieces of past image information are recorded in the radiation solid-state detector 10. The correction means 50 includes an elapsed time calculation means 70. The elapsed time calculation means 70 acquires a time T2 when image information intended to be currently read is recorded, and calculates a plurality of elapsed times from the recording times of the above plurality of pieces of past image information and the recording time of the image information intended to be currently read according to the plurality of time T1's recorded and the above time T2. The correction means 50 has the past image signals Xn in accordance with the plurality of elapsed times $\Delta t_n$, and certain coefficients $a_n$ calculated based on the past image signals Xn and the elapsed times $\Delta t_n$ in a look up table (LUT) shown in FIG. 4. Each certain coefficient $a_n$ is a function of Xn as well as a function of $\Delta t_n$, and is expressed as $a_n = a_n(Xn)$. The coefficient $a_n$ is calculated for each pixel signal in the past image signal. The above described correction processing is performed for each pixel based on the coefficient $a_n$ calculated for each pixel. Note that the memory means 60 and the elapsed time calculation means 70 are provided in the correction means 50, but may be provided separately from the correction means 50.

Next, a description will be made for a method of recording radiation image information as an electrostatic latent image in the radiation solid-state detector 10 with the present radiation image recording and reading apparatus, and reading the recorded electrostatic latent image. First, an electrostatic latent image recording process will be described with reference to a charge model shown in FIGS. 3A to 3C. In the drawing, the negative and positive charges produced in the recording photosensitive layer 12 with the recording light L1 are represented by the circled symbols "−" and "+" respectively. The following description will show a general process of recording and reading a radiation image in the present radiation image recording and reading apparatus, but will not particularly consider the effect of the residual charges due to the past radiation image information recorded.

Figure 3A:
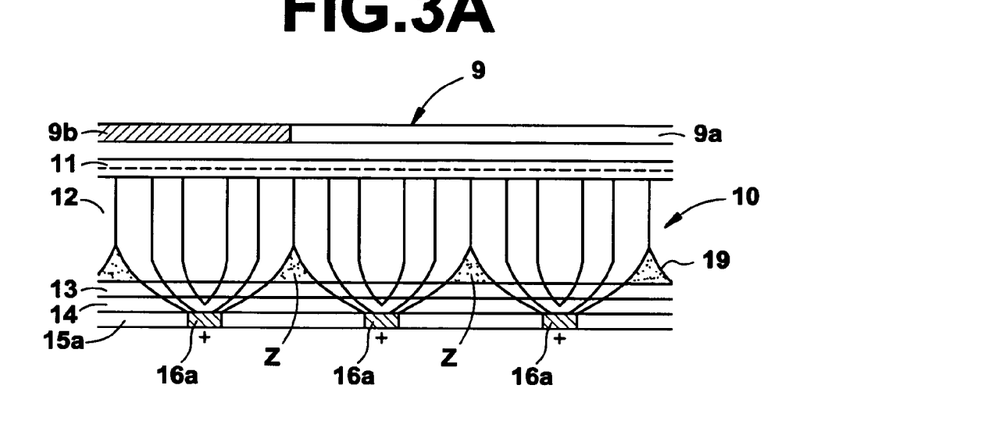
FIGS. 3A, 3B and 3C are views illustrating a method of recording an electrostatic latent image in the above described radiation solid-state detector.

In recording the electrostatic latent image in the radiation solid-state detector 10 by use of the present radiation image recording and reading apparatus, a direct current voltage is applied between the first electrode layer 11 and the stripe electrode 16, both of which are electrified. Accordingly, a substantially U-shaped electric field is formed between the first electrode layer 11 and the stripe electrode 16, and there is a substantially parallel electric field in most part of the recording photoconductive layer 12. However, in the interface between the photoconductive layer 12 and the charge transport layer 13, namely in the electric accumulator 19, there are some parts where no electric field exists Z. Then, an electric field distribution where the U-shaped electric field is continuous in the longitudinal direction of the elements 16a is formed (FIG. 3A).

Figure 3B:
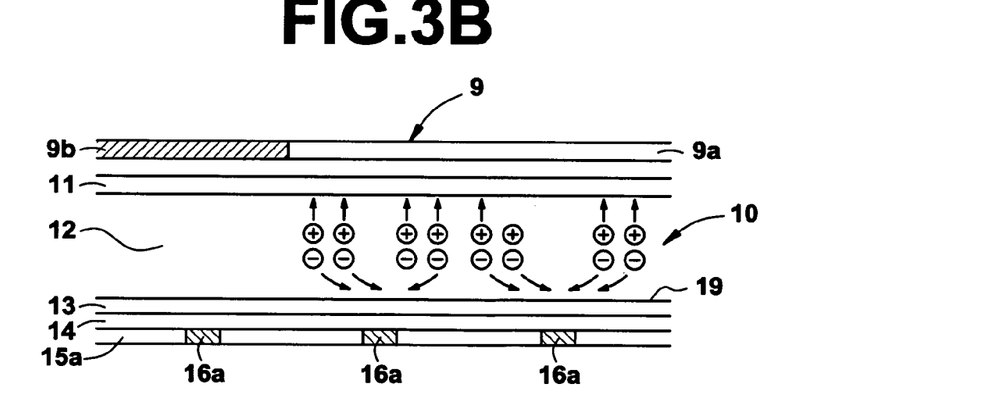
Figure 3C:
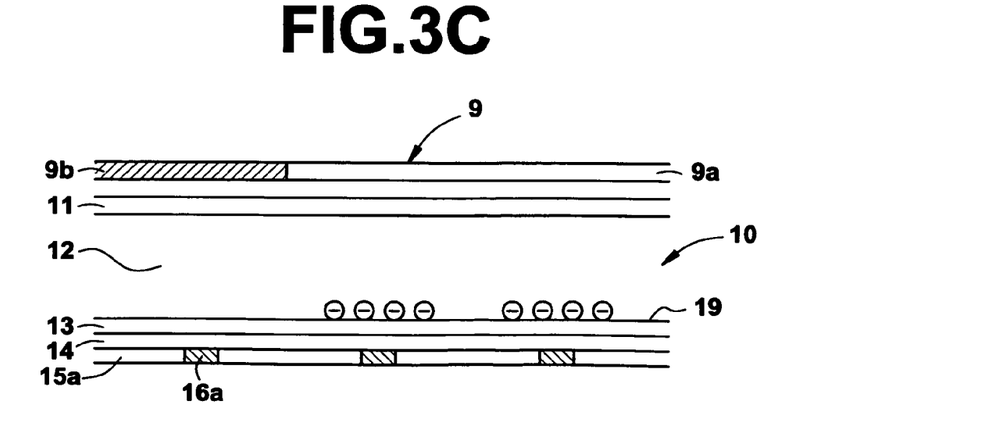

Subsequently, the radiation is irradiated on the object 9, and the recording light L1 that is transmitted through the transparent part 9a of the object 9 and holds the radiation image information of the object 9 is irradiated on the radiation solid-state detector 10. Accordingly, pairs of negative and positive charges are produced in the recording photoconductive layer 12 of the radiation solid-state detector 10. The negative charges among the produced charges move to the electric accumulator 19 along the above described electric field distribution (FIG. 3B). On the other hand, the positive charges produced in the recording photoconductive layer 12 move toward the first electrode layer 11 at high speed. In the interface between the first electrode layer 11 and the recording photoconductive layer 12, the positive charges are then recombined with negative charges charged in the first electrode layer 11 and disappear. Since the recording light L1 is not transmitted through the opaque part 9b of the object 9, no change occurs in part of the radiation solid-state detector 10 corresponding to the opaque part 9b (FIGS. 3B and 3C).

In this way, by the irradiation of the recording light L1 on the object 9, the charges in accordance with an image of the object can be accumulated in the electric accumulator 19 which is the interface between the recording photoconductive layer 12 and the charge transport layer 13. The quantity of the accumulated latent image charges (negative charges) is substantially proportional to the dose of the radiation, which is transmitted through the object 9, and then incident on the radiation solid-state detector 10. Accordingly, the latent image charges hold the electrostatic latent image, and the electrostatic latent image is recorded in the radiation solid-state detector 10.

Next, an electrostatic latent image reading process by the present radiation image recording and reading apparatus will be described. In reading the electrostatic latent image from the radiation solid-state detector 10, the first electrode layer 11 and the stripe electrode 16 are short-circuited by virtual short circuits of the current detection amplifiers in the current detection circuit 40, and the charges are rearranged. Subsequently, by the sub scanning in the longitudinal direction (sub scanning direction) of the elements 16*a* with the reading light irradiation means 30, the radiation solid-state detector 10 is scanned and exposed to the linear reading light L2. Such scanning exposure with the reading light L2 produces pairs of negative and positive charges in the part of the photoconductive layer 14 corresponding to the sub scanning position where the reading light L2 is incident.

An electric field (intense electric field) is formed between the electric accumulator 19 and the stripe electrode 16, and the charge transport layer 13 acts as a conductor for positive charges. Accordingly, the positive charges produced in the reading photoconductive layer 14 move at high speed through the charge transport layer 13 attracted to the latent image charges of the electric accumulator 19. The positive charges are then recombined with the latent image charges in the electric accumulator 19 and disappear. On the other hand, the negative charges produced in the reading photoconductive layer 14 are recombined with the positive charges of the first electrode layer 11 and the stripe electrode 16 and disappear. Change in voltage between the first electrode layer 11 and the stripe electrode 16 caused by the above charge recombination is detected by the current detection amplifiers as change in current. The current flowing in the radiation solid-state detector 10 during the reading corresponds to the latent image charges, namely, the electrostatic latent image. Accordingly, the pixel signal of each pixel can be obtained by detecting the current with the current detection amplifier.

In the recording and reading processes of the radiation image as described above, considering the effect of the residual charges produced by the radiation image information recorded in the past, the pixel signal read in such a manner is smaller than the pixel signal in accordance with the radiation image information actually recorded in the radiation solid-state detector 10 because of decrease in the charge conversion efficiency in the recording photoconductive layer 12 and decrease in the reading efficiency in the reading photoconductive layer 14.

In order to solve the above described problem, the present radiation image recording and reading apparatus is provided with the correction means 50. In the correction means 50, correction processing is performed for the above described pixel signal based on the past image signal in accordance with the past image information and the elapsed time between the recording time of the past image information and the recording time of the radiation image information intended to be currently read. Note that, in the embodiment, it is assumed that the past image information is read immediately after the recording of the same, and that there is little loss in the past image information between the recording time and the reading time of the past image information. Accordingly, the above described elapsed time may be an elapsed time from the reading time of the past image information to the recording time of the image radiation information intended to be currently read.

Figure 5:
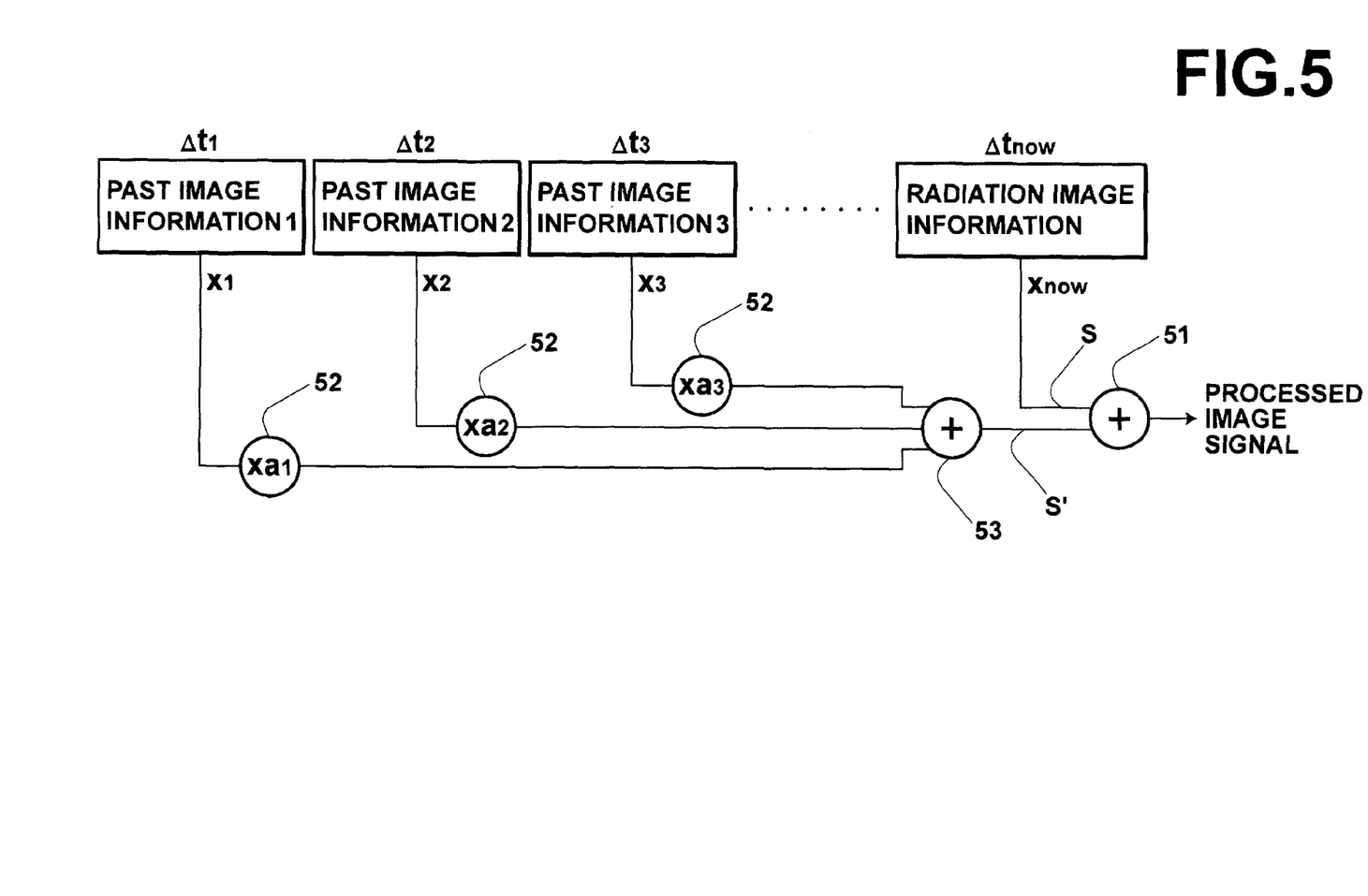
FIG. 5 is a view illustrating the correction processing in the correction means.

In the correction means 50, a pixel signal S for each pixel in accordance with the radiation image information intended to be currently read is stored and the pixel signal S is outputted to a first adder 51 (see FIG. 5). On the other hand, based on the plurality of past image signals previously stored and the plurality of elapsed times calculated for the respective past image signals, the certain coefficients $a_n$ are determined with reference to the LUT shown in FIG. 4. Each of the past image signals in accordance with the coefficient $a_n$ is multiplied by the coefficient $a_n$ in each multiplier 52. Results thereof are outputted to a second adder 53 and added up. The correction signal S' obtained by the addition in the second adder 53 is outputted to the first adder 51, where the correction signal S' is added to the pixel signal S for each pixel and outputted as a processed pixel signal. Each processed pixel signal is subjected to a certain image processing or the like in the following step, and then used for constituting the reproduced image. In the above described correction processing, only the pixel signals corresponding to the pixels with the radiation image information are subjected to the correction processing. For example, the pixel where the pixel signal is smaller than a certain value is not subjected to the above correction processing as the pixel is treated as the one without the radiation image information.

In the above described embodiment, each piece of the past image information is read immediately after the recording of the same. However, in a case where the interval from the time of recording the past image information in the solid-state detector to the time of reading the same is long and the amount of loss of the recorded past image information during the interval is not negligible, the correction is performed based on the above amount of loss and the past image signal by using the time period from the time of recording the past image information from the solid-state detector to the time of recording the current image information as the elapsed time. The above described amount of loss may be calculated based on the time period from the time of recording the past image information in the solid-state detector to the time of reading the same and the radiation dose or the signal value at the time of recording the past image information in the solid-state detector.

According to the above described radiation image recording and reading apparatus, the past image signals, which are read for the past image information recorded in the radiation solid-state detector 10 before the image information intended to be currently read in the solid-state detector, and the time T1's as the times of recording the past image information in the radiation solid-state detector 10 are recorded. Then the time T2 as the time of recording the above described image information is acquired. Based on the time T1's and the time T2, the elapsed times from the respective recording times of the past image information and the recording time of the above described image information are calculated. The pixel signals are then corrected based on the past image signals and the elapsed times. Accordingly, in recording the past radiation image information, it is possible to suppress degradation of the image quality such as the S/N ratio of the reproduced image, the degradation being caused by the effect of the charges which are produced by exposure with excessive radiation and remain in the radiation solid-state detector or the like.

The correction means 50 determines the coefficients $a_n$ based on the past image signals and the elapsed times, and corrects the current image signal based on the coefficients $a_n$ and the past image signals. Accordingly, the signal size in accordance with the residual charges in recording the radiation image information intended to be currently read can be calculated more accurately, and thus more accurate correction can be performed.

Not only in the above described radiation image information recording and reading apparatus using the radiation solid-state detector which records the radiation image by converting radiation into charges, but also in the radiation image information recording and reading apparatus using a radiation solid-state detector where the radiation image is recorded by the fluorescence emitted by exposure to radiation, the correction processing similar to the above described processing can suppress degradation of the image quality such as the S/N ratio of the reproduced image caused by decrease in the efficiency of converting radiation into fluorescence, the decrease being caused by exposure of excessive radiation in recording the past radiation image information.

Furthermore, in the above described radiation image recording and reading apparatus, the radiation solid-state detector of the optical reading type is utilized, but the radiation solid-state detector is not limited to this type, and may be a radiation solid-state detector of the TFT reading type.

What is claimed is:

1. A method of reading an image for reading an image signal, which comprises a plurality of image pixels, in accordance with image information from a solid-state detector, where the image information is recorded by exposure to a recording electromagnetic wave holding the image information, the method comprising the steps of:

storing a plurality of past image signal read regarding past image information, each past image signal comprising a plurality of past image pixels, which are recorded in the solid-state detector before the image information is recorded in the solid-state detector, and a times T1~Tn as times of recording the past image information in the solid-state detector or a time of reading the past image information from the solid-state detector;

acquiring a time T' as a time of recording the image information;

calculating elapsed times corresponding to each past image signal from times of recording the past image information or times of reading the past image information to the time of recording the image information based on the time T1~Tn and the time T';

calculating independently certain coefficients for each past image pixel based on the past image signals and the elapsed times corresponding thereto;

correcting independently each current image pixel of the current image signal based on the certain coefficients and the plurality of past image signals and elapsed times to corresponding to each past image signal; and reproducing the image based on the corrected current image signal;

wherein the elapsed times are not based on a predetermined constant time interval.

2. The method of claim 1, wherein correcting the current image signal takes into account effects of residual charges in the solid-state detector.

3. The method of claim 1, wherein the time T1 corresponds to a time for recording the past image signal in the detector.

4. The method of claim 1, wherein correcting the current signal comprises addition of differently weighted signals of the past image signals with the current image signal.

5. An image reading apparatus including a solid-state detector for accumulating charges produced by exposure to a recording electromagnetic wave holding image information to record the image information, and a reading means for reading an image signal in accordance with the image information recorded in the solid-state detector, the image reading apparatus comprising:

a memory means for storing a plurality of past image signals, each comprising a plurality of past image pixels, read regarding past image information by the reading means, the past image information being recorded in the solid-state detector before the image information is recorded in the solid-state detector, and times T1~Tn as times of recording the past image information in the solid-state detector or times of reading the past image information from the solid-state detector;

an elapsed time calculation means for acquiring a time T' as a time of recording the image information and calculating elapsed times corresponding to each past image signal from times of recording the past image information or times of reading the past image information to the time of recording the image information based on the time T1~Tn and the time T';

a correction means for correcting the current image signal, which comprises a plurality of current image pixels, based on the plurality of past image signals stored in the memory means and elapsed times to corresponding to each past image signal; and means for reproducing the image based on the corrected current image signal, wherein the correction means calculates independently for each past image pixel certain coefficients based the past image signals and the elapsed times corresponding thereto, and corrects independently the current image pixels of the current image signal based on the certain coefficients and the past image signals;

wherein the elapsed times are not based on a predetermined constant time interval.

6. The image reading apparatus according to claim 5, wherein the memory means stores past image signals regarding a plurality of pieces of past image information recorded at different times, and the time T1's regarding the respective past image signals;

the elapsed time calculation means calculates a plurality of elapsed times from the times of recording the plurality of pieces of past image information or the times of reading the plurality of pieces of past image information to the time of recording the image information based on the plurality of time T1's and the time T'; and said correction means corrects the current image signal based on the plurality of past image signals and the plurality of elapsed times.

7. The image reading apparatus according to claim 6, wherein the reading means includes:

a linearly extending light source;

a scanning mechanism for performing scanning with the linear light source in a direction substantially orthogonal to a longitudinal direction of the linear light source; and a stripe electrode including a plurality of linear electrodes arranged in the longitudinal direction, the linear electrodes linearly extending and taking out the charges produced by scanning, the scanning being performed with the linear light source in the substantially orthogonal direction by the scanning mechanism.

8. The image reading apparatus according to claim 6, wherein the reading means includes:

a number of TFT switches for taking out the charges as the image signal; and a control unit for controlling the TFT switches.

9. The image reading apparatus according to claim 5, wherein the reading means includes:
 a linearly extending light source;
 a scanning mechanism for performing scanning with the linear light source in a direction substantially orthogonal to a longitudinal direction of the linear light source; and
 a stripe electrode including a plurality of linear electrodes arranged in the longitudinal direction, the linear electrodes linearly extending and taking out the charges produced by scanning, the scanning being performed with the linear light source in the substantially orthogonal direction by the scanning mechanism.

10. The image reading apparatus according to claim 5, wherein the reading means includes:
 a number of TFT switches for taking out the charges as the image signal; and
 a control unit for controlling the TFT switches.

11. The apparatus of claim 5, wherein the correction means takes into account effects of residual charges in the solid-state detector.

12. The apparatus of claim 11, wherein the effects of residual charges is not constant.

* * * * *